(12) United States Patent
Vilser et al.

(10) Patent No.: US 7,284,860 B2
(45) Date of Patent: Oct. 23, 2007

(54) UNIVERSAL OPHTHALMIC EXAMINATION DEVICE AND OPHTHALMIC EXAMINATION METHOD

(75) Inventors: Walthard Vilser, Rudolstadt (DE);
Bernd-Ullrich Seifert, Griesheim (DE);
Christine Kassner, Ilmenau (DE)

(73) Assignee: Imedos GmbH, Jena (DE)

( * ) Notice: Subject to any disclaimer, the term of this patent is extended or adjusted under 35 U.S.C. 154(b) by 397 days.

(21) Appl. No.: 11/003,647

(22) Filed: Dec. 3, 2004

(65) Prior Publication Data
US 2005/0122475 A1 Jun. 9, 2005

(30) Foreign Application Priority Data
Dec. 5, 2003 (DE) ................................. 103 57 734

(51) Int. Cl.
*A61B 3/10* (2006.01)
(52) U.S. Cl. ...................... 351/205; 351/206; 351/246
(58) Field of Classification Search ......... 351/200–247
See application file for complete search history.

(56) References Cited
U.S. PATENT DOCUMENTS

| | | | | |
|---|---|---|---|---|
| 4,580,559 A | * | 4/1986 | L'Esperance | ................... 606/3 |
| 4,838,679 A | * | 6/1989 | Bille | ........................... 351/205 |
| 6,478,424 B1 | * | 11/2002 | Grinvald et al. | ............ 351/206 |

FOREIGN PATENT DOCUMENTS

| | | |
|---|---|---|
| DE | 196 48 935 | 5/1998 |
| DE | 10151314 | 4/2003 |
| DE | 10313975 | 11/2003 |
| EP | 1 100 370 | 6/2002 |

* cited by examiner

*Primary Examiner*—Scott J. Sugarman
*Assistant Examiner*—James R Greece
(74) *Attorney, Agent, or Firm*—Reed Smith LLP

(57) ABSTRACT

A universal ophthalmic examination device and an ophthalmic examination method have the object of combining in an inexpensive apparatus in a simple manner the device-related requirements for image generation, measurement and functional imaging for carrying out visual stimulation and highly time-resolved and highly spatially resolved image documentation using continuous illumination and flash mode and the requirements for measurements in the infrared spectral region and visible spectral region with a time regime that can be freely selected to a great extent. The light of at least one light source is modified in a program-oriented manner with respect to its intensity curve and/or time curve with a temporally defined relationship to the adjustments of the at least one light source, of the image recording and of the evaluation for purposes of adaptive matching to an examination task in the illumination beam path by an individual, shared light manipulator and is used as modified light for illumination and for selective stimulation.

23 Claims, 1 Drawing Sheet

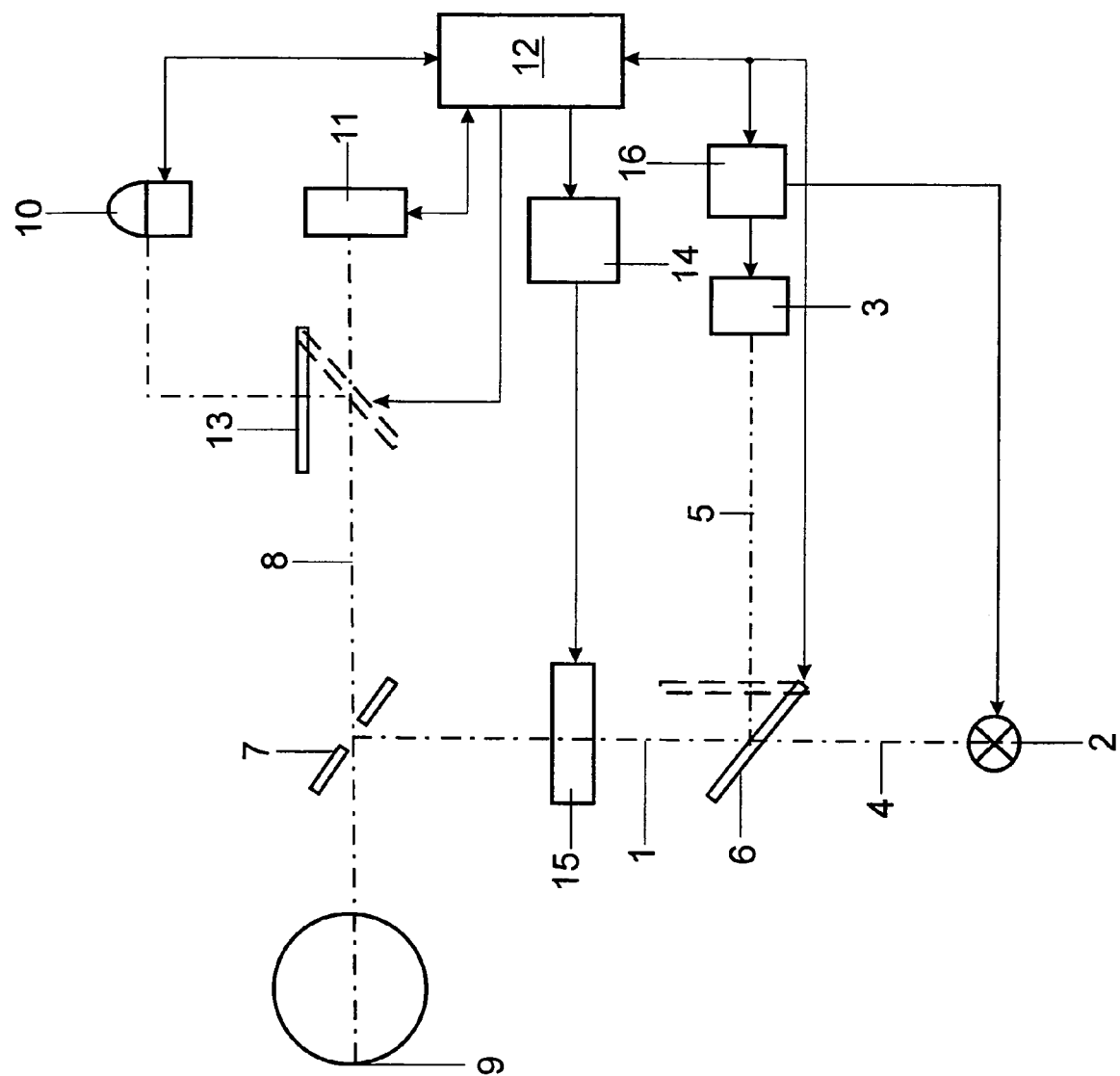

UNIVERSAL OPHTHALMIC EXAMINATION DEVICE AND OPHTHALMIC EXAMINATION METHOD

CROSS-REFERENCE TO RELATED APPLICATION

This application claims priority of German Application No. 103 57 734.3, filed Dec. 5, 2004, the complete disclosure of which is hereby incorporated by reference.

BACKGROUND OF THE INVENTION a) Field of the Invention

The invention is directed to a universal ophthalmic examination device which has, in combination with a central control unit, at least one primary light source in an illumination beam path directed to an object being examined and at least one image recording and evaluating unit for documenting and/or for measuring at least partial areas of the object being examined, and electronically switchable elements for beam path switching.

The invention is further directed to an ophthalmic examination method in which an object to be examined is illuminated and selectively stimulated by an illumination beam path for recording images with light of at least one light source and in which examination results are derived by recording images of the object to be examined and evaluating the images obtained by the image recording.

The invention is applicable in diagnostic systems in which image generation, measurement, stimulation and functional imaging of the eyeground or ocular fundus are component parts of the examination of the human and animal eye. In particular, systems of this type include ophthalmoscopes, mydriatic and non-mydriatic retinal cameras, systems for vascular analysis and measurement of various other quantities of microcirculation, metabolism, circulation time by means of indicator technique, blood velocity (LDV, LDF) and spectrometric data at the fundus that are based on direct or indirect ophthalmoscopy.

b) Description of the Related Art

Known image-generating systems use flash devices or continuous light sources as illumination systems.

While image documentation in flash mode generates high-quality images, the succession in time on individual images per second is limited in terms of technique and also with respect to the light stress for patients. In addition, devices with flash beam paths are cost-intensive and lead to an increase in structural size and weight.

Continuous illumination, on the other hand, enables continuous sequences of image recordings, e.g., in video mode, but the images have only a low geometric resolution and poor image quality because of the light stress limit and the continuous illumination itself.

While stepping up the control of the lamps that are used improves the image quality with reasonable light burden, the flickering of the light that is caused by the inertia of the lamp and is perceptible to the patient leads to corresponding anticipatory attitudes, blinking, squinting and eye movements which again leads to considerable impairment of image quality.

Further, it is known to display stimulated (provoked) topographic measurements in fundus images. By means of functional imaging, as it is called, it can be observed on the basis of the time curve of the response reaction of the retinal vessels how the autoregulation mechanism attempts to eliminate the disturbance (provocation) through changes in vascular diameter.

Apart from stimulation, functional imaging also requires high-quality image generation and measurement; it should also be ensured as far as possible that time allocation is free and that it is possible to change rapidly between image generation, stimulation and measurement. Combination with infrared illumination is useful for reducing the light burden on the patient, e.g., during stimulation with light.

A known device according to EP 1 100 370 B1 is based on the use of functional changes in retinal reflectivity in which light of a stimulating illuminator is blended into the beam path in addition to the continuous illumination to induce a detectable function response signal. The light of the two separate beam paths can be alternately switched or superimposed.

In this arrangement, stimulation is used to change the structure and light-scattering characteristics of determined layers of the retina. Since the biological response is seen in the diffuse reflection of the retinal structures, this device is oriented to the examination of changes in radiation characteristics in that changes in diffuse reflection are compared and documented by generating differential images for two different function states.

Although this offers the advantage that the light from any light sources can be superimposed or alternately switched, it is disadvantageous that stimulation necessitates another device whose light must be brought to the retina on an additional beam path by means of a splitter mirror.

When structures at the ocular fundus are measured for function diagnostic examinations instead of using functional changes in retinal reflectivity, DE 196 48 935 A1 offers a system which is suitable for blood vessels that are visually accessible or can be imaged in some other manner and by which the essential relevant clinical function diagnostic characteristic quantities can be determined and displayed with high reproducibility and minimal stress on the patient. For provocation, flickering light can be provided in a separate beam path and is superimposed on the continuous measurement light. Since the modified flash beam path serves as a separate beam path, there is the disadvantage that high-quality image documentation by means of flash light for functional imaging is discarded.

OBJECT AND SUMMARY OF THE INVENTION

It is the primary object of the invention to combine in an inexpensive apparatus in a simple manner the device-related requirements for image generation, measurement and functional imaging for carrying out visual stimulation and highly time-resolved and highly spatially resolved image documentation using continuous illumination and flash mode and the requirements for measurements in the infrared and visible spectral region with a time regime that can be freely selected to a great extent.

According to the invention, this object is met in an examination device of the type mentioned above in that an optical light manipulator which communicates with the central control unit and which is jointly controllable is arranged in the illumination beam path provided for the at least one primary light for program-oriented modification of the intensity curve and/or time curve of the primary light in a temporally defined relationship with the adjustments of the primary illumination and of the image recording and evaluation, and in that a secondary light that is generated from the primary light by means of the modification is provided for illumination and for selective stimulation of the object to be examined.

Further, the above-stated object is met, according to the invention, by an ophthalmic examination method mentioned in the beginning in that the light of the at least one light source is modified in a program-oriented manner with respect to its intensity curve and/or time curve with a temporally defined relationship to the adjustments of the at least one light source, of the image recording and of the evaluation for adaptive matching to an examination task in the illumination beam path and is used as modified light for illumination and for selective stimulation.

By influencing the illumination by means of an individual element arranged in the illumination beam path, multifunctionality can be achieved in that the characteristics of the light in the illumination beam path are changed so as to be adapted to function, so that there is no need for a separate stimulating illuminator that is blended in through an additional beam path.

The invention makes it possible to generate images of measurable structures from induced function response signals in an adaptive manner and therefore to build an ophthalmic examination device which is considerably improved with respect to scope of application. Adaptive matching also means that feedback to the computer control can be produced from signals that are derived from the examination results or formed as sensor signals in order to optimize the control of the light manipulator and of the intensity curve and/or time curve and the control of the primary illumination and of the image recording and evaluation in a result-oriented manner. By means of light-induced stimulation of changes in the retinal microcirculation, vasodilations or changes in other quantities of microcirculation, e.g., oxygen saturation and blood velocity can be determined directly or indirectly with the ophthalmic examination device based on the images.

The freely programmable control of the light modulator determines whether the light of the primary source is used for illumination or for stimulation. Image generation and measurement can be carried out even during the stimulation.

In addition to optimizing known applications, the invention, above all, makes possible completely new applications of systems for imaging and measuring the ocular fundus through the use of adaptive control.

DESCRIPTION OF THE FEATURES OF THE INVENTION

Flash Operation with Continuous Illumination

When the light manipulator is carried out, e.g., as a fast electrooptic switch, bright continuous observation light of the retinal camera can be reduced optionally and can be stepped up to any higher intensity in the manner of a flash at a desired time so as to be synchronized with the image recording. Delays which formerly occurred when controlled directly due to the inertia of the lamp no longer play a role. This provides the advantage that the continuous illumination device can also be used for a flash-like illumination with considerably improved image quality and, at the same time, the light stress on the fundus for adjusting processes and measuring processes is considerably reduced.

In order to reduce output losses, the lamp of the continuous illumination device can be operated with reduced output during the adjusting process. At the moment of triggering, before the actual image recording, the electrooptic switch which is based on a variable transmission can be reduced with respect to its transmission to the extent that the output of the lamp is increased while the illumination intensity at the fundus remains constant. The electrooptic switch is moved to the transparent state for the desired exposure time synchronous with the image recording only after reaching the light intensity required for high-quality recording. Following this, the adjusting operation can be produced again with reduced lamp output in reverse sequence.

Adaptive Fluorescence Angiography

When continuous image recording or measurement is required, e.g., with only 5 images rather than with the full frame rate, the illumination beam path can be released only during the desired images with corresponding synchronization of the controllable optical light manipulator. The light stress on the ocular fundus is considerably lower or, with the light burden remaining the same, substantially more light is available for the recording in the individual selected images. Interesting applications result for video angiography in which the time sequence of illuminated images and intensity can be adapted to the medical interrogation. This realization according to the invention means that the examiner can produce an image sequence with different characteristics that is completely relevant to the examination. Formerly, this was not possible. Since the actual exposure time is given in this case by the illumination time, images with a high irradiation intensity on the eye can be generated in very short time intervals and any time sequence with any illumination intensity and image recording time can be adjusted. When the control of the image recording camera or of a plurality of image recording cameras in different switchable beam paths is incorporated in the control, it is possible to adapt the time resolution, photometric resolution and geometric resolution of the images to the examination processes in any desired manner and the entire system can be provided with a previously unknown functional adaptivity. At the same time, the high adaptivity of the examination device according to the invention can be used for adapting to individual peculiarities of the eye in order to optimize the diagnostic quality and the image quality and to minimize error sources such as eye movements. Examples include changing between high-resolution individual images and continuous recording with rest pauses for the eye for displaying autofluorescence in the idle phase, premature and delayed arterial flow-in phase with high time resolution, e.g., in short double-image sequences for displaying blood velocity, with longer double-image sequences for displaying capillary blood velocity, the full phase with highly photometrically resolved and highly time-resolved individual images, a longer rest pause for the flow-out phase and photometric high-sensitivity recording of images from the post-phase for displaying dye exits which then only require a low temporal and spatial resolution.

Combination of Static and Dynamic Vascular Analysis and Parallel High-Resolution Image Recording as Image Documentation Parallel to Measurements for Functional Imaging Another substantial advantage consists in that measurements with continuous light can be carried out with a low light burden, e.g., for the dynamic vascular analysis with a device constructed in accordance with DE 196 48 935 A1, during which high-quality images for static vascular analysis can be recorded at desired programmable times by means of a flash-type control of the illumination light within the measuring process.

The flashed image can be recorded with the same camera that was used to carry out the measurements or in another beam path with another camera. Whereas in the first case the sensitivity of the camera must be adapted immediately prior to the flashed image recording, in the second case the second recording channel must be opened along the other beam path so as to be synchronized with the controllable optical light manipulator.

Further, the flash can be generated by the controllable optical light manipulator from the continuous illumination or with the flash illumination device by itself or with a flash of the flash illumination device that is modified by the controllable optical light manipulator.

Flickering Light

When continuous light is used for measurement, the controllable optical light manipulator can be used for light interruption so as to be synchronized with the image recording and can generate flickering light. The measurements can continue during the flickering light in the respective bright images. Therefore, the flickering light provocation which is important for function diagnostics, e.g., of vessels, can be realized with different frequencies.

Increased Dynamic Range of Continuous Vide Recordings

Another advantage is the quasi-continuous image recording of objects with substantially different diffuse reflection like the papilla and macula. When the illumination intensity is changed suddenly, e.g., from frame to frame, the macula or papilla are obtained correctly illuminated alternately for purposes of measurement and assessment in the image.

Another very useful effect for increasing the dynamic range is obtained when the control of the image signal is determined and fed back to the control unit of the optical light manipulator. In this case, e.g., during fluorescence angiography in the different fluorescence phases, the brightness can be controlled in such a way that an optical image control is achieved with minimum light burden in connection with the amplification of the image signal. The high dynamic range with respect to time between the very dark idle recordings and the very bright images in the full phase lead to local overradiation or glare in the images which can be prevented with the invention.

Flash Reduction

Another advantageous effect can be achieved by modifying the flash of the flash illumination device by means of cutting out flash portions with respect to time with the controllable optical light manipulator, so that the flash time can be shortened depending on the switching speed of the light manipulator. Sine shorter flash times reduce eye movements during the flash, sharper images result.

Further, with correspondingly short flash times, an effect occurs whereby the movement of the red blood cell columns can be resolved.

Double-Flash for Speed Mapping

The flash modification with the controllable optical light manipulator can also be carried out in such a way that two flash portions are cut out of a flash. When it is ensured, by means of synchronizing the flash times for image recording, that image recordings are carried out during the two partial flashes, the resulting images contain resolved blood cell flows from which displacement vectors and speed fields can be calculated. Surprisingly, the invention ensures a speed mapping in a simple manner.

IR Nonmyd

Another surprising effect results through the use of an optical light modulator which switches only the visible spectral range and is transparent for the infrared spectral range. When the switching of the light modulator is synchronized with an infrared camera, provided as an alternative, and a camera for the visible spectrum with blocked infrared, both mydriatic retinal cameras and non-mydriatic cameras can be used. This results in the further advantage that vascular analysis and functional imaging can be carried out as non-mydriatic examinations.

Simple Insertion, Retrofit

The optical light modulator can also be inserted in the illumination beam path as a multifunctional element by means of a filter insert which exists already in the commercially available retinal camera, so that this filter insert can be retrofitted economically and without time-consuming modifications of the existing structural and optical configurations. The required connections from the electronically controllable devices to the control and evaluation computer and adapted programming are to be carried out corresponding to the above-described applications to be realized.

The invention will be described more fully in the following with reference to the schematic drawing.

BRIEF DESCRIPTION OF THE DRAWING

The drawing is a block diagram showing a construction of an ophthalmic examination device according to the invention in the form of a flash-enabled retinal camera for measurements in the infrared range and retinal stimulation by means of flickering light.

DESCRIPTION OF THE PREFERRED EMBODIMENTS

The examination device has an illumination beam path 1 serving as a common beam path for an illumination device 2 which radiates continuously in the visible and infrared range and which is constructed as a halogen lamp and a flash illumination device 3. The light of the two illumination devices 2 and 3 can be coupled into the illumination beam path 1 alternatively along separate beam paths 4 and 5 by means of a tilting mirror 6.

A pinhole mirror 7 is inserted in the illumination beam path 1. An imaging beam path 8 passes through the central opening of the pinhole mirror 7 and the illumination light is directed to the ocular fundus 9 over the area surrounding the central opening by means of optically imaging elements, not shown. Light reflected by the ocular fundus 9 travels along the imaging beam path 8 and via optically imaging elements, again not shown, for the image recording. For this purpose, in the present embodiment example, two image recording devices 10 and 11 are provided whose camera controls are connected to a central control unit, e.g., a computer 12 and, depending on the examination task, can be provided alternatively for image recording by a tilting mirror 13 which is likewise computer-controlled.

According to the invention, a controllable optical light manipulator 15 that is connected to an electronic control module 14 interfacing with the computer 12 is arranged in the illumination beam path 1. It is also possible to combine the light modulator 15 with different filters.

The light manipulator 15 is a shared element that is available to all of the illumination devices and generates secondary light by modifying the light of at least one primary light source, in this case, the continuously radiating illumination device 2 and the flash illumination device 3.

A power supply 16 which serves to supply power to the two illumination devices 2 and 3 is also connected to the computer 12, likewise the two tilting mirrors 6 and 13.

The controllable optical light manipulator 15 acts in such a way that the primary illumination bundle can be modified in many different ways with respect to time and intensity in a program-oriented manner. The light that is modulated in this way is used for the realization of different advantageous functions of the examination device, wherein the modulation is controlled in relation to the parameters of the primary illumination (in this case, continuous illumination and flash), the image recording and the evaluation.

Of course, the controllable optical light manipulator 15 can be constructed in different forms and, as in the present case, can be a component based on variable transmission. However, components whose reflection characteristics can be changed in a program-oriented manner in connection with a correspondingly adapted beam path are also usable.

It is particularly advantageous for the results of examination and with respect to the light burden on the eye that the intensity curve and time cure of the continuous illumination and of an individual flash can be manipulated in any desired manner not only during the exposure time for an image but also between image sequences, since this considerably expands the scope of functionality.

When a continuous vascular analysis, for example, is to be carried out with the ophthalmic examination device according to the invention by infrared illumination and with the simultaneous possibility of applying light stimulus in the form of a full-field flickering, the image recording device 10 for image acquisition is to be constructed as an infrared-sensitive electronic camera and is to be provided with a blocking filter for visible light.

In this application, the image recording device 11 can be used to record high-resolution fundus images, on the basis of which examination results obtained in the infrared range can be correlated topographically, if necessary, in a comprehensible manner.

A continuous vascular analysis using infrared illumination is based on the illumination of the fundus with infrared light of the halogen lamp with simultaneous image acquisition with the infrared-sensitive electronic camera. The tilting mirror 6 for this task is connected in such a way that the beam path 4 for the continuous light is conveyed in the illumination beam path 1, from which the light travels via the light manipulator 15 and the pinhole mirror 7 to the object to be examined, that is, the ocular fundus.

The light manipulator 15 which is based on a variable transmission is constructed as a fast electrooptic switch, e.g., based on a transmissive LC shutter, whose optical characteristics are a high transmission for infrared light and a transmission for visible light that can be switched on and off.

For the examination mentioned above, the light manipulator 15 blocks the visible component of the illumination light during the rest phases and is switched to transmission for photo-provocation. The light reflected by the ocular fundus is guided through the opening in the pinhole mirror 7 along the imaging beam path 8 and via the tilting mirror 13 to the image recording device 10 which sends its images continuously to the central control unit. The adjustment of the entire system can be monitored permanently by means of a control monitor, not shown.

For vascular analysis, the vessel portions to be examined are either marked interactively at the control monitor or are detected automatically by the image processing software of the central control unit. Measurement of the vessel portions is carried out in the continuous image flow.

During the stimulation phases, the light modulator 15 can be controlled with freely selectable signal shapes and frequencies so that correspondingly modulated visible light reaches the ocular fundus 9. Due to sensitivity exclusively to infrared light, the image acquisition of the image recording unit 10 is not impaired by this modulation, so that vessel measurement can be carried out by the central control unit during rest phases as well as stimulation phases.

When a high-resolution fundus image is to be recorded during the infrared examination to show the measurement locations topographically and to correlate measurement results, a rest phase is used in order to switch the flash illumination beam path 5 to the common illumination beam path 1 with the tilting mirrors 6 and 13 or to direct the imaging beam path 8 to the image recording device 11. When the light modulator 15 is switched so as to be transparent for visible light, the flash lamp of the flash illumination device 3 and the image recording device 11 are triggered simultaneously.

Alternatively, the entire examination can be carried out in visible light. The light manipulator 15 is then constructed for optimal vessel contrast as a combined electrooptic switch and suitable bandpass filter. The image acquisition is carried out by means of the image recording unit 11. In order to enable image recording during the stimulation phase, the light modulator 15 is controlled with a synchronized square-wave signal (full-field flicker). The flickering frequency is then dependent on the frame rate of the camera that is used. For a CCD video camera (PAL standard), the continuous image flow at a synchronized flicker frequency of 12.5 Hz alternately comprises a correctly exposed image and a quasi-unexposed image. Longer or shorter periods of the synchronized stimulation signal are possible as even-number multiples or portions of the duration of a frame.

While the foregoing description and drawings represent the present invention, it will be obvious to those skilled in the art that various changes may be made therein without departing from the true spirit and scope of the present invention.

What is claimed is:

1. A universal ophthalmic examination device for examination of the eyeground comprising, in combination with a central control unit:
   a light source in an illumination beam path directed to the eyeground being examined;
   at least one image recording and evaluating unit for documenting and/or for measuring at least partial areas of the eyeground;
   electronically switchable elements for beam path switching;
   an optical light manipulator which communicates with the central control unit and which being jointly controllable being arranged in the illumination beam path provided for the light for program-oriented modification of the intensity curve and/or time curve of primary light generated by the light source in a temporally defined relationship with the adjustments of an eyeground illumination and of an image recording and evaluation controlling; and
   a secondary light that is generated from the primary light by the modification being provided for simultaneously complete illumination of the eyeground for the purpose of recording images of measurable retinal structures and for selective light-induced stimulation of changes in the retinal microcirculation.

2. The ophthalmic examination device according to claim 1, wherein the optical light manipulator is an electrooptic component based on a controllably variable transmission.

3. The ophthalmic examination device according to claim 1, wherein the optical light manipulator is fastened to a carrier which can be introduced into the illumination beam path and removed from the illumination beam path.

4. The ophthalmic examination device according to claim 1, wherein a continuously radiating illumination device is provided as the primary light source.

5. The ophthalmic examination device according to claim 4, wherein the continuously radiating illumination device comprises at least the visible and infrared spectral range.

6. The ophthalmic examination device according to claim 5, wherein the optical light manipulator is an electrooptic component that is based on a controllably variable transmission in the visible spectral range and is transparent in the infrared spectral range, in that separate recording channels are provided for the visible spectral range and infrared spectral range, and in that a switching element for controlling the switching which serves to switch between the recording channels is connected to the central control unit.

7. The ophthalmic examination device according to claim 1, wherein the optical light manipulator is an electrooptic component which is based on a controllably variable reflection.

8. The ophthalmic examination device according to claim 1, wherein an optical sensor is connected to the central control unit for obtaining control signals for the central control unit.

9. The ophthalmic examination device according to claim 1, wherein a second primary light source is constructed as a flash illumination device.

10. The ophthalmic examination device according to claim 9, wherein light radiated by the flash illumination device is directed in part to an optical sensor for detecting the starting edge of a flash and for forming a switching signal for purposes of adaptive control.

11. The ophthalmic examination device according to claim 1, wherein a flash illumination device is provided as primary light source.

12. An ophthalmic examination method including the steps of: illuminating the eyeground and selectively stimulating changes in the retinal microcirculation of the eyeground in a light-induced manner by an illumination beam path for recording images with light;
    deriving examination results by recording images of the eyeground and evaluating the images obtained by the image recording; and
    generating the light for illumination and selective stimulation of changes in the retinal microcirculation from a single light source by light in a program-oriented manner with respect to its intensity curve and/or time curve with a temporally defined relationship to the adjustments of the light source, of the image recording controlling and of the evaluation for adaptive matching to an examination task in the illumination beam path.

13. The ophthalmic examination method according to claim 12, wherein, for purposes of adaptive matching, feedback to the computer control is produced from signals that are derived from the examination results or formed as sensor signals in order to optimize the control of the intensity curve and or time curve and the control of the at least one light source and of the image recording and evaluation in a result-oriented manner.

14. The ophthalmic examination method according to claim 12, wherein the light of a continuously radiating light source is initially reduced in intensity and is stepped up to a higher intensity at a desired time so as to be synchronized with the image recording.

15. The ophthalmic examination method according to claim 12, wherein the continuously radiating light source is increased in output while the intensity of the light is reduced for retaining a constant illumination strength for the object under examination, and in that the intensity of the light is increased in a flash-generating manner when reaching an output of the light source that is necessary for high-quality image recordings.

16. The ophthalmic examination method according to claim 12, wherein a control of the image sequence and or of the change in quality of the image content is carried out by the modification of the intensity curve and/or time curve.

17. The ophthalmic examination method according to claim 12, wherein a flash-generating control of the light intensity is carried out at selected times when recording images with illumination by the continuously radiating light source.

18. The ophthalmic examination method according to claim 17, wherein the image recordings are carried out with continuous light in the infrared spectral region while the flash generation is carried out in the visible spectral region.

19. The ophthalmic examination method according to claim 18, wherein the image recordings with continuous illumination and with flash-generated illumination are carried out in the same image recording channel.

20. The ophthalmic examination method according to claim 18, wherein the image recordings with continuous illumination and with flash-generated illumination are carried out in separate image recording channels.

21. The ophthalmic examination method according to claim 12, wherein flickering light is generated from the light of the continuously radiating light source by interruption of light, wherein the bright phases are used for carrying out measurements.

22. The ophthalmic examination method according to claim 12, wherein at least a portion from a flash of a flash illumination device serving as light source is cut out with respect to time by modifying the time curve.

23. The ophthalmic examination method according to claim 22, wherein images with time-resolved content are produced by synchronization of the flash times of the cut out flash portions for image recording.

* * * * *